United States Patent [19]

Wallner et al.

[11] Patent Number: 4,879,224

[45] Date of Patent: Nov. 7, 1989

[54] DNA SEQUENCES, RECOMBINANT DNA MOLECULES AND PROCESSES FOR PRODUCING HUMAN PHOSPHOLIPASE INHIBITOR POLYPEPTIDES

[75] Inventors: Barbara P. Wallner, Cambridge; R. Blake Pepinsky, Watertown; Jeffrey L. Garwin, Bedford, all of Mass.

[73] Assignee: Biogen, Inc., Cambridge, Mass.

[21] Appl. No.: 690,146

[22] Filed: Jan. 10, 1985

[51] Int. Cl.[4] .................. C12N 1/14; C12N 1/16; C12N 5/00; C12N 7/00; C12N 15/00; C12N 1/20; C07H 21/00; C12P 21/00

[52] U.S. Cl. .................. 435/68; 435/235; 435/320; 435/252.31; 435/252.33; 435/252.34; 435/252.35; 435/254; 435/255; 435/240.2; 435/240.4; 536/27; 935/11; 935/27; 935/31; 935/72

[58] Field of Search .......... 435/68, 172.3, 240, 435/243, 253, 254, 252, 320, 235; 536/27; 935/11, 14, 27, 28, 29, 30, 31, 32, 34, 35, 37, 38, 41, 67, 68, 69, 70, 71, 72, 73, 74, 75

[56] References Cited

U.S. PATENT DOCUMENTS

| | | | |
|---|---|---|---|
| 4,239,780 | 12/1980 | Wallach | 424/330 |
| 4,394,443 | 7/1983 | Weissman et al. | 435/68 X |
| 4,530,901 | 7/1985 | Weissmann | 435/320 X |
| 4,537,858 | 8/1985 | O'Sullivan et al. | 435/119 |

FOREIGN PATENT DOCUMENTS

WO86/06100 10/1986 World Int. Prop. O. ............ 435/68

OTHER PUBLICATIONS

Huang, K. et al, *Cell*, vol. 46, pp. 191–199, Jul. 18, 1986.
Fava, R. et al, *J. Biol. Chem.*, vol. 259, pp. 2636–2645, Feb. 24, 1984.
Wallner, B. et al, *Nature*, vol. 320, pp. 77–81, Mar. 6, 1986.
Pepinsky, R. et al, *J. Biol. Chem.*, vol. 261, pp. 4239–4246, Mar. 25, 1986.
Pepinsky, R., *J. Biol. Chem.*, vol. 258, pp. 11229–11235, 1983.
Oroszlan, S. et al, *Proc. Natl. Acad. Sci.*, vol. 75, pp. 1404–1408, 1978.
D. M. et al, *Prostaglandins*, vol. 28, pp. 441–442, 1984.
Pepinsky, R. et al, *Nature*, vol. 321, pp. 81–84, 1986.
G. S. Blackwell et al., "Glucocorticoids Induce the Formation and Release of Anti-Inflammatory and Anti--Phospholipase Proteins Into the Peritoneal Cavity of the Rat", *Br. J. Pharmac.*, 76, pp. 185–194 (1982).
F. F. Davidson et al., "Inhibition of Phospholipase $A_2$ by Lipocortins and Calpactins", *J. Biol. Chem.*, 262, pp. 1698–1705 (1987).
P. Dimond, "Biogen Produces Recombinant Anti-Inflammatory Agent", *Genetic Engineering News*, 5, p. 12 (1985).
E. Erickson et al., "Identification of a Cellular Protein Substrate Phosphorylated by the Avian Sarcoma Virus Transforming Gene Product", *Cell*, 21, pp. 829–836 (1980).
E. Erickson et al., "Biochemical Characterization of a 34 Kilodalton Normal Cellular Substrate of $pp60^{v-src}$ and an Associated 6 Kilodalton Protein", *Mol. Gen. Biol.*, 4, pp. 77–85 (1984).
M. Errasfa et al., "The Presence of Lipocortin in Human Embryonic Skin Fibroblasts and its Regulation by Anti-Inflammatory Steroids", *Biochemica et Biophysica Acta*, 847, pp. 247–254 (1985).

(List continued on next page.)

*Primary Examiner*—Jayme A. Huleatt
*Attorney, Agent, or Firm*—James F. Haley, Jr.; Denise L. Loring; David J. Meyer

[57] ABSTRACT

DNA sequences, recombinant DNA molecules and hosts transformed with them which produce human phospholipase inhibitor polypeptides and methods of making and using these products. The DNA sequences and recombinant DNA molecules are characterized in that they code on expression for a human phospholipase inhibitor polypeptide. In appropiate hosts these DNA sequences permit the production of human phospholipase inhibitor polypeptides.

9 Claims, 6 Drawing Sheets

OTHER PUBLICATIONS

Etienne and J. Polonovski, "Phospholipase A$_2$ Activity in Rat and Human Lymphocytes", *Biochem. and Biophys. Res. Comm.*, 125, pp. 719-727 (1984).

R. J. Flower and G. J. Blackwell, "Anti-Inflammatory Steroids Induce Biosynthesis of a Phospholipase A$_2$ Inhibitor Which Prevents Prostaglandin Generation", *Nature*, 278, pp. 456-459 (1979).

R. J. Flower et al., "Macrocortin and the Mechanism of Action of the Glucocorticoids", *Advances in Inflammation Research*, 7, pp. 61-70 (1984).

M. J. Geisow, "Common Domain Structure of Ca$^{+2}$ and Lipid Binding Proteins", *FEBS Letters*, 203, pp. 99-103 (1986).

M. J. Geisow and J. H. Walker, "New Proteins Involved in Cell Regulation by Ca$^{+2}$ and Phospholipids", *Trends Biochem. Sci.*, 11, pp. 420-423 (1986).

V. Gerke and K. Weber, "Identity of p36K Phosphorylated Upon Rous Sarcoma Virus Transformation With a Protein Purified from Brush Borders; Calcium-Dependent Binding to Non-Erythroid Spectrin and F-Actin", *EMBO Journal*, 3, pp. 227-233 (1984).

V. Gerke and K. Weber, "Calcium-Dependent Conformational Changes in the 36-kDa Subunit of Intestinal Protein I Related to the Cellular 36-kDa Target of Rous Sarcoma Virus Tyrosine Kinase", *J. Biol. Chem.*, 260, pp. 1688-1695 (1985).

J. R. Glenney and B. F. Track, "Amino-Terminal Sequence of p36 and Associated p10: Identification of the Site of Tyrosine Phosphorylation and Homology with S-100", *Proc. Nat. Acad. Sci U.S.A.*, 82, pp. 7884-7888 (1985).

T. Hattori, et al., "Inhibition of Human Natural Killer (NK) Activity and Antibody Dependent Cellular Cytotoxicity (ADCC) by Lipomodulinn, A Phospholipase Inhibitory Protein", *Chem. Abstr.*, 99, #86478r (1983), IBID *J. Immunol.*, 131, pp. 662-665 (1983).

F. Hirata et al., "A Phospholipase A$_2$ Inhibitory Protein in Rabbit Neutrophils Induced by Glucocorticoids", *Proc. Nat. Acad. Sci. U.S.A.*, 77, pp. 2533-2536 (1980).

F. Hirata, "The Regulation of Lipomodulin, A Phospholipase Inhibitory Protein, In Rabbit Neutrophils by Phosphorylation", *J. Biol. Chem.*, 256, pp. 7730-7733 (1981).

F. Hirata et al., "Presence of Autoantibody For Phospholipase Inhibitory Protein, Lipomodulin, in Patients With Rheumatic Disease", *Proc. Nat. Acad. Sci. U.S.A.*, 78, pp. 3190-3194 (1981).

F. Hirata et al., "Identification of Several Species of Phospholipase Inhibitory Protein(s) By Radioimmunoassay For Lipomodulin", *Biochem. Biophys. Res. Comm.*, 109, pp. 223-230 (1982).

F. Hirata, "Roles of Lipomodulin: A Phospholipase Inhibitory Protein In Immunoregulation", *Chem. Abstr.*, 100 #119189s (1984).

F. Hirata, "Roles of Lipomodulin: A Phospholipase Inhibitory Protein in Immunoregulation", *Adv. Inf. Res.*, 7, pp. 71-78 (1984).

F. Hirata et al., "Inhibition of Leukocyte Chemotaxis by Glu-Glu-Glu-Glu-Tyr-Pro-Met-Glu and Leu-Ile-Glu-Asp-Asn-Glu-Tyr-Thr-Ala-Arg-Gln-Gly", *Biocem. and Biophys. Res. Comm.*, 118, pp. 682-690 (1984).

F. Hirata et al., "Isolation and Characterization of Lipocortin (Lipomodulin)", *Agents and Actions*, 17, pp. 263-266 (1985).

R. H. Kretsinger et al., "Consensus in Exocytosis", *Nature*, 320, p. 573 (1986).

I. Mancheva et al., "The Primary Structure of the Inhibitor of Vipoxin From the Venom of the Bulgarian Viper *Vipera ammodytes ammodytes*, Serpentes)", *Hoppe-Selye's Z. Physiol. Chem.*, 365, pp. 885-894 (1984).

I. Mancheva et al., "Sequence Homology Between Phospholipase and its Inhibitor in Snake Venom: The Primary Structure of the Inhibitor of Vipoxin From the Venom of the Bulgarian Viper", *Biol. Abstr.*, 79, #39874 (1984).

T. Maniatis et al., *Molecular Cloning a Laboratory Manual*, pp. 5-6, 405-14 (1984).

J. F. Morrow, "Recombinant DNA Techniques", *Methods in Enzymology*, 68, pp. 3-24 (1979).

K. Radke et al., "Transformation by Rous Sarcoma Virus: A Cellular Substrate for Transformation-Specific Protein Phosphorylation Contains Phosphotyrosine", *Cell*, 21, pp. 821-828 (1980).

C. J. M. Saris et al., "The cDNA Sequence For the Protein-Tyrosine Kinase Substrate p36 (Calpactin I Heavy Chain) Reveals a Multidomain Protein With Internal Repeats", *Cell*, 46, pp. 201-212 (1986).

"Biogen Produces Anti-Inflammatory Agent: Davies Resigns," *Genetic Engineering Letter*, p. 4, Jun. 1985.

FIG. 1

CNBr 1: (less than 2 Kd based on amino acid analysis)

- met - lys - gly - ala - gly - thr - arg - arg - lys - thr -
  1     2     3     4     5     6     7     8     9     10 leu - ile -
  11    12

CNBr 2: (less than 2 Kd based on amino acid analysis)

- met - leu - lys - thr - pro - ala - gln - phe - asp - ala -
  1     2     3     4     5     6     7     8     9     10 asp - glu - leu - ile(?) - arg(?)
  11    12    13    14        15

CNBr 3: (7 Kd based on SDS-polyacrylamide gel electrophoresis)

- met - $\frac{tyr}{lys}$ - $\frac{val}{ala}$ - asn - gln - asp - $\frac{leu}{trp}$ - ala - $\frac{ala}{gln}$ -
  1      2           3           4     5     6      7           8       9

CNBr 4: (no protein detected by SDS-PAGE)

CNBr 5: (mixture of peptides, less than 5 Kd based on SDS-PAGE)

CNBr 6: (mixture consisting of two 12 Kd fragments based on SDS-PAGE)

FIG. 2

T17(a+b):  $-\dfrac{ala}{tyr} - \dfrac{leu}{phe} - \dfrac{gln}{val} - \dfrac{gln}{gln} - \dfrac{ala}{lys} - \dfrac{tyr}{gly} - gln - \dfrac{arg}{gly}$
                   1           2            3            4            5            6          7          8

T22(a):    - ser - glu - ile - asp - met - asn - glu - ile - lys
             1     2     3     4     5     6     7     8     9

T22(b):    - lys - val - phe - gln - asn - tyr - arg
             1     2     3     4     5     6     7

T23:       - ser - tyr - pro - his(arg) - leu
             1     2     3       4         5

T24:       - thr - pro - ala - gln - phe - asp - ala - asp - glu -
             1     2     3     4     5     6     7     8     9
             leu - leu - arg
              10    11    12

T29:       - ala - ala - tyr - leu - gln - glu - thr - gly - lys -
             1     2     3     4     5     6     7     8     9
             pro - leu - asp - glu - thr - leu - lys
              10    11    12    13    14    15    16

T31:       - gly - gly - pro - gly - ser - ala - val - ser - pro -
             1     2     3     4     5     6     7     8     9
             tyr - pro - ser(thr) - phe - asn - ser(thr) - ser -
              10    11      12        13    14      15      16
             ser - thr - val - ala - trp - ala -
              17    18    19    20    21    22

T35:       - lys - gly - thr - asp - val - asn - val - phe(?) -
             1     2     3     4     5     6     7      8
             asn - thr -  x  - leu
              9    10    11    12

T38:       - gly - leu - gly - thr - asp - glu -
             1     2     3     4     5     6

FIG. 3

Sequence T22a:  GluILeAspMetAsnGluIle
    20-mer      GARATHGAYATGAAYGARAT

Sequence T22b:  LysValPheGlnAsnTyr
    17-mer      AARGTNTTYCARAAYTA

Sequence T24[1]: AlaGlnPheAspAlaAspGlu
    20-mer      GCNCARTTYGAYGCNGAYGA

Sequence T29:   GlnGluThrGlyLysPro
    17-mer      CARGARACNGGNAARCC

[1] The sequence shown for T24 is also contained within CNBr fragment 2.

Coding redundancies are:

```
    1  TTCTCTTTAGTTCTTTGCAAGAAGGTAGAGATAAAGACACTTTTTCAAAAATGGCAATGGTATCAGAATTCCTCAAGCAGGCCTGGTTTATTGAAAATG
       ----------------------------------------------------------------------------------------------------

101  AAAGAGAAATCAAGAAACGTTCTTCCATCTCTATTCTCTGAAAAAGTTTTACCGTTACCATAGTTCTTAAGGAGTTCGTCCGGACCAAATAACTTTTAC
       ----------------------------------------------------------------------------------------------------
       PheLeuPheSerSerLeuGlnGluGlyArgAsplysThrPheSerLysMetAlaSerGluPheLeuLysGlnAlaTrpPheIleGluAsnG 201  AAGAGCAGGAATATGTTCAAACTGTGAAGTCATCCAAAGGTGGTCCCGGATCAGCGGTGAGCCCCTATCCTACCTTCAATCCATCCTGGATGTCCTGC
       ----------------------------------------------------------------------------------------------------

301  TTCTCGTCCTTATACAAGTTTGACACTTCAGTAGGTTCCACCAGGGCCTAGTCGCCACTCGGGATGGAAGTTAGTAGGAGCCTACACCACG
       ----------------------------------------------------------------------------------------------------
       luGluGlnGluTyrValGlnThrValLysSerLysGlyGlyProGlySerAlaValSerProTyrProThrPheAsnProSerSerAspValAlaAl

401  CTTGCATAAGGCCATAATGGTTAAAGGTGTGGATGAAGCAACCATCATTGACATTCTAACTAAGCGAAACAATGCACAGCTCAACAGATCAAGCAGCA
       ----------------------------------------------------------------------------------------------------

501  GAACGTATTCCGGTATTACCAATTCCACCACTTCGTTGGTAGTAACTGTAAGATTGATTGGTTGTTACGTGTCGCAGTTGTCTAGTTCTCGT
       ----------------------------------------------------------------------------------------------------
       aLeuHisLysAlaIleMetValLysGlyValAspGluAlaThrIleIleAspIleLeuThrLysArgAsnAsnAlaGlnArgGlnIleLysAlaAla

601  TATCTCCAGGAAACAGGAAAGCCCCTGGATGAAACACTTAAGAAGGCCCTTACAGGTCACCTTGAGGAGGTTGTTTTAGCTCTGTAAAAACTCCAGCGC
       ----------------------------------------------------------------------------------------------------

701  ATAGAGGTCCTTTGTCCTTTCGGGACCTACTTGTGAATTCTTGAACTCCAGTGGAACTCCTCCAACAAAATCGAGACGATTTTGAGGTCGCG
       ----------------------------------------------------------------------------------------------------
       TyrLeuGlnThrGlyLysProLeuAspGluThrLeuLysLysAlaLeuThrGlyHisLeuGlyValValLeuAlaLeuLeuLysThrProAlaG

801  AATTTGATGCTGATGAACTTCGTGCTGCCATGAAGGGCCTGGAACTGATGAAGATACTCTAATTGAGATTTTGGCATCAAGAACTAACAAAGAATCAG
       ----------------------------------------------------------------------------------------------------

901  TTAAACTACGACTACTTGAAGCACGACGACTTCCCGGAACCTACTCTTGACTACTTCTATGAGATTAACTCTAAAACCGTAGTTCTTGTTCTTTAGTC
       ----------------------------------------------------------------------------------------------------
       lnPheAspAlaAspGluLeuArgAlaAlaMetLysGlyLeuArgAlaAspLeuGlyThrLeuIleGluIleLeuAlaSerArgThrAsnLysGluIleAr

1001  AGACATTAACAGGGTCTACAGAGAGGAACTGAAGAGAGATCTGGCCAAAGACATAACCTCAGACACATCTGGAGATTTTCGGAACGCCTTGCTTCTCTT
       ----------------------------------------------------------------------------------------------------

1101  TCTGTAATTGTCCCAGATGTCTCTCCTTGACTTCTTCTAGACCGGTTCTGTATTGGAGTCTGTGTAGACCTCTAAAAGCCTTGCGAACGAAGAGAA
       ----------------------------------------------------------------------------------------------------
       gAspIleAsnArpValTyrArgGluGluLeuLysArgAspLeuAlaLysAspIleThrSerGlyAspPheArgAsnAlaLeuSerLeu

1201  GCTAAGGGTGACCGATCTGAGGACTTTGGTGTGAATGAAGACTTGCTGATTCAGATGCCAGGGCCTTGTATGAAGCAGGAGGAAAGGAGAAGGGACAG
       ----------------------------------------------------------------------------------------------------

1301  CGATTCCCACTGGCTAGACCTGGAAACCACACTTCTGAACCGACTAAGTCTACCGACCGTCCCCGGAACATACTTCTCCTTTCCCTCCTTCCCCTGTC
       ----------------------------------------------------------------------------------------------------
       AlaLysGlyAspArgSerGluAspPheGlyValAsnGluAspLeuAlaArgSerAspAlaArgAlaLeuTyrGluAlaGlyGluArgLysGlyThrA
```

FIG. 4 (cont'd)

```
      ACGTAAACGTCTTCAATACCATCCTTACCACCAGAAGCTATCCACAACTTCCGCAGAGTGTTCAGAAATACCAAGTACAGTAAGCATGACATGAACAA       800
701   ----------------------------------------------------------------------------------------------------
      TGCATTGCACAAGTTATGGTAGGAATGGTGGTCTTCGATAGTGTTGAAGCGCTCCACAAAGTCTTTATGTGGTTCATCTGTTCTCATTCGTACTTCTT
      spValAsnValPheAsnThrIleLeuThrThrArgSerTyrProGlnLeuArgValPheGlnLysTyrThrLysTyrSerLysHisAspMetAsnLy

AGTTCTGGACCTGGAGTTGAAAGGTGACATTGAGAAATGCCTCACAGCTATCGTGAAGTGCCGCCACAAGCAAACCAGCTTTCTTTGCAGAGAAGCTTCAT       900
801   ----------------------------------------------------------------------------------------------------
      TCAAGACCTGGACCTCAACTTCCACTGTAACTCTTTACGGAGTGTCGATAGCACTTCACGCGGGTGTCGTTGGTCGAAAGAAACGTCTCTTCGAAGTA
      sValLeuAspLeuGluLeuLysGlyAspIleGluLysCysLeuThrAlaIleValLysCysArgHisLysGlnThrSerLysProAlaPhePheAlaGluLysLeuHis

CAAGCCATGAAAGGTGTTGGAACTCGCCATAAGGCATTGATCAGGATTATGGTTCCCCTTCTGAAATTGACATGAATCAAGCATTCTATCAGA              1000
901   ----------------------------------------------------------------------------------------------------
      GTTCGGTACTTTCCACAACCTTGAGCGGTATTCCGTAACTAGTCCTAATACCAAAGGGCAAGACTTTAACTGTACTTACTATAGTTTCCTAAGATAGTCT
      GlnAlaMetLysGlyValGlyThrArgHisLysAlaLeuIleArgIleMetValSerArgSerGluIleAspMetAsnAspIleLysAlaPheTyrGlnL

AGATGTATGGTATCTCCCCTTGCCAAGCCATCCTGATGAAACCAAAGGAGATTATGAGAAAATCCTGCTCTTTGTGGAGGAAAACATTCCC              1100
1001  ----------------------------------------------------------------------------------------------------
      TCTACATACCATAGAGGGAACGGTTCGGTAGGACCTACTTTGGTTCCTCTAATACTCTTTTAGGACCACCGAGAAACACCTCCTTTGATTGTAAGGG
      ysMetTyrGlyIleSerLeuCysGlnAlaIleLeuAspGluThrLysGlyIleAlaIleLeuArgIleLeuValAlaLeuCysGlyAsnEnd

TTGATGGTCTCAAGCTATGATCAGAAGACTTTAATTATATATTTCATCCTATAAGCTTAAATAGGAAAGTTTCTCAACAGGATTACAGTGTAGCTACC           1200
1101  ----------------------------------------------------------------------------------------------------
      AACTACCAGAGTTCGATACTAGTCTTCTGAAATTAATATATAAAGTAGGATATTCGAATTTATCCTTTCAAAGAAGTTGTCCTAATGTCACATCGATGC

TACATGCTGAAAATATAGCCTTTAAATCATTTTTATATTATAACTCTGTATAATAGAGATAAGTCCATTTTTTAAAAATGTTTTCCCCAAACCATAAAA        1300
1201  ----------------------------------------------------------------------------------------------------
      ATGTACGACTTTTTATATCGGAAATTTAGTAAAAATATTGAGACATATTATCTCTATTCAGGTAAAAATTTTACAAAAGGGTTTGGTATTTTT

CCCTATACAAGTTGTTCTAGTAACAATACATGAGAAAGATGTCTATGTAGCTCGAAAATAAAATGACGTCACAAGAC                            1376
1301  ----------------------------------------------------------------------------------------------------
      GGGATATGTTCAACAAGATCATTGTTATGTACTTCTCTACAGATACATCGACTTTTATTTTACTGCAGTGTTCTG
```

FIG. 5

DNA SEQUENCES, RECOMBINANT DNA MOLECULES AND PROCESSES FOR PRODUCING HUMAN PHOSPHOLIPASE INHIBITOR POLYPEPTIDES

TECHNICAL FIELD OF THE INVENTION

This invention relates to DNA sequences, recombinant DNA molecules and processes for producing at least one human phospholipase inhibitor protein. More particularly, the invention relates to DNA sequences and recombinant DNA molecules that are characterized in that they code for at least one human phospholipase inhibitor-like polypeptide. Accordingly, hosts transformed with these sequences may be employed in the processes of this invention to produce the human phospholipase inhibitor-like polypeptides of this invention. These polypeptides possess anti-inflammatory activity and are useful in the treatment of arthritic, allergic, dermatologic, ophthalmic and collagen diseases.

BACKGROUND OF THE INVENTION

Arachidonic acid is an unsaturated fatty acid that is a precursor in the synthesis of compounds, such as prostaglandins, hydroxy-acids and leukotrines, that are involved in inflammation reactions. It is released from membrane phospholipids by phospholipase $A_2$ activity. In response to anti-inflammatory agents, such as glucocorticoids, certain cells release proteins that have been characterized in vitro by their ability to inhibit phospholipase $A_2$. Accordingly, by inhibiting arachidonic acid production, phospholipase inhibitor proteins block the synthesis of prostaglandins and other inflammatory substances, thereby reducing inflammation [F. Hirata et al., "A Phospholipase $A_2$ Inhibitory Protein In Rabbit Neutrophils Induced By Glucocorticoids", Proc. Natl. Acad. Sci. U.S.A., 77, No. 5, pp. 2533–36 (1980)].

To date, several phospholipase $A_2$ inhibitory proteins have been studied. One of them—lipomodulin—has been characterized as an about 40,000 molecular weight protein that is probably degraded by proteases in the cell to two smaller active species of about 30,000 and 15,000 molecular weight [F. Hirata et al., "Identification Of Several Species Of Phospholipase Inhibitory Protein(s) By Radioimmunoassay For Lipomodulin", Biochem. Biophys. Res. Commun., 109, No. 1, pp. 223–30 (1982)]. Other experimental evidence suggests that two other phospholipase $A_2$ inhibitors, macrocortin (about 15,000 molecular weight) and renocortin (two species with molecular weights of about 15,000 and 30,000 respectively) may also be cleavage products of larger inhibitory proteins such as lipomodulin [J. F. Cloix et al., "Characterization And Partial Purification Of Renocortins: Two Polypeptides Formed In Renal Cells Causing The Anti-Phospholipase-like Action Of Glucocorticoids", Br. J. Pharmac., 79, pp. 313–21 (1983); G. J. Blackwell et al , "Macrocortin: A Polypeptide Causing The Anti-Phospholipase Effect of Glucocorticoids", Nature, 287, pp. 147–49 (1980)].

Although lipomodulin has been isolated from rabbit neutrophil cells, macrocortin from rat macrophages and renocortin from rat renomedullary interstitial cells, the three proteins exhibit similar biological activities, molecular weights and cross-reactivity with monoclonal antibodies against lipomodulin or macrocortin. Moreover, all are induced by glucocorticoids. Thus, it has been suggested that these phospholipase inhibitory proteins are closely related to each other and are produced by cells as a general physiological mechanism of steroid action [B. Rothhut et al., "Further Characterization Of The Glucocorticoid-Induced Antiphospholipase Protein 'Renocortin'", Biochem. Biophys. Res. Commun., 117, No. 3, pp. 878–84 (1983)].

Recent data have also indicated that the 15,000 molecular weight species of lipomodulin is produced by lymphocytes in response to immunogens and acts as a glycosylation-inhibiting factor, inhibiting the glycosylation of IgE-binding factors and leading to the suppression of the IgE response [T. Uede et al., "Modulation Of The Biologic Activities Of IgE-Binding Factors: I. Identification Of Glycosylation-Inhibitory Factor As A Fragment of Lipomodulin", J. Immunol., 130, No. 2, pp. 878–84 (1983)].

As a result of their anti-inflammatory activities, phospholipase inhibitor proteins are useful for the treatment of disorders involving inflammatory processes. Such disorders include arthritic, allergic, dermatologic, ophthalmic and collagen diseases. Furthermore, the use of these proteins to treat inflammation might avoid the disadvantages now associated with present anti-inflammatory compounds.

At present two classes of compounds are being used for anti-inflammatory therapy: corticosteroids and non-steroidal anti-inflammatory drugs. Corticosteroids are generally disfavored due to the severe side effects that may be associated with their use. These effects include hypertension, gastrointestinal bleeding, muscle weakness, cataracts and convulsions. Thus, nonsteroidal anti-inflammatory compounds are preferred. However, these non-steroids may also produce side effects, such as adverse effects on gastric and platelet physiology and on the central nervous system and hematopoesis.

Because phospholipase inhibitor proteins are only mediators of steroid action, it is unlikely that they will produce the side effects often associated with the use of corticosteroids. Furthermore, because these inhibitor proteins are natural mediators produced by the cell, they are unlikely to have the side effects usually associated with many nonsteroid anti-inflammatories.

To date, however, human phospholipase inhibitor proteins have not been purified from cells. Furthermore, even if a procedure could be developed for the purification of phospholipase inhibitors, it is doubtful that sufficient quantities of them could be produced for their many clinical and commercial applications. Accordingly, processes enabling the production of human phospholipase inhibitor proteins in clinically useful amounts would be highly advantageous in anti-inflammatory therapy.

SUMMARY OF THE INVENTION

The present invention solves the problems referred to above by providing DNA sequences coding for at least one human phospholipase inhibitor-like polypeptide and processes for producing such polypeptides in hosts transformed with those DNA sequences.

The DNA sequences of this invention are selected from the group consisting of the cDNA insert of λLC, DNA sequences which hybridize to that cDNA insert and which code on expression for a human phospholipase inhibitor-like polypeptide, and DNA sequences which code on expression for a polypeptide coded for on expression by any of the foregoing DNA sequences. Recombinant DNA molecules containing these DNA sequences, hosts transformed with them and human phospholipase inhibitor-like polypeptides coded for on expression by them are also part of this invention.

The DNA sequences, recombinant DNA molecules, hosts and processes of this invention enable the production of human phospholipase inhibitor-like polypeptides for use in the treatment of arthritic, allergic, dermatologic, ophthalmic and collagen diseases, as well as their diseases, involving inflammation processes.

DETAILED DESCRIPTION OF THE INVENTION

In order that the invention herein described may be more fully understood, the following detailed description is set forth.

In the description the following terms are employed:

Nucleotide--A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence--A linear array of nucleotides connected one to the other by phosphodiester bonds between the 3' and 5' carbons of adjacent pentoses.

Codon--A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame--The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TGT AAG—Ala—Gly—Cys—Lys

G CTG GTT GTA AG—Leu—Val—Val

GC TGG TTG TAA G—Trp—Leu—(STOP)

Polypeptide--A linear array of amino acids connected one to the other by peptide bonds between the α-amino and carboxy groups of adjacent amino acids.

Genome--The entire DNA of a cell or a virus. It includes inter alia the structural gene coding for the polypeptides of the substance, as well as operator, promoter and ribosome binding and interaction sequences, including sequences such as the Shine-Dalgarno sequences.

Gene--A DNA sequence which encodes through its template or messenger RNA ("mRNA") a sequence of amino acids characteristic of a specific polypeptide.

Transcription--The process of producing mRNA from a gene or DNA sequence.

Translation--The process of producing a polypeptide from mRNA.

Expression--The process undergone by a gene or DNA sequence to produce a polypeptide. It is a combination of transcription and translation.

Plasmid--A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($TET^R$) transforms a cell previously sensitive to tetracycline into one which is resistant to it. A cell transformed by a plasmid is called a "transformant".

Phage or Bacteriophage--Bacterial virus many of which consist of DNA sequences encapsidated in a protein envelope or coat ("capsid").

Cosmid--A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

Cloning Vehicle--A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning--The process of obtaining a population of organisms or DNA sequences derived from one such organism or sequence by asexual reproduction.

Recombinant DNA Molecule or Hybrid DNA--A molecule consisting of segments of DNA from different genomes which have been joined end-to-end outside of living cells and able to be maintained in living cells.

Expression Control Sequence--A sequence of nucleotides that controls and regulates expression of genes when operatively linked to those genes. They include the lac system, the β-lactamase system, the trp system, the tac and trc systems, the major operator and promoter regions of phage λ, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

Phospholipase Inhibitor-Like Polypeptide -- A polypeptide displaying a biological or immunological activity of a phospholipase inhibitor protein. This polypeptide may include amino acids in addition to those of a native phospholipase inhibitor protein or it may not include all of the amino acids of native phospholipase inhibitor protein. Finally, it may include an N-terminal methionine.

The present invention relates to DNA sequences and recombinant DNA molecules coding for human phospholipase inhibitor-like polypeptides and processes for the production of those polypeptides.

Although a variety of selection and DNA cloning techniques might potentially have been employed in our isolating and cloning of a DNA sequence of this invention, we adopted a selection strategy based upon rat phospholipase $A_2$ inhibitor protein. Accordingly, we purified a rat phospholipase $A_2$ inhibitor protein from the extracellular supernatant of rat peritoneal exudate cells and determined the amino acid sequence of various fragments of that protein. Based on those protein sequences, we then synthesized several antisense oligonucleotide DNA probes corresponding to those regions of purified rat protein which had minimal nucleotide degeneracy. We then used these probes to screen a human cDNA library comprising *E. coli* cells containing human macrophage cDNA sequences inserted into a phage cloning vector.

For screening, we hybridized the oligonucleotide probes to the human cDNA library utilizing a plaque hybridization screening assay and we selected clones hybridizing to a number of our probes. After isolating and subcloning the selected human cDNA inserts into plasmids, we determined their nucleotide sequences and compared them to our amino acid sequences from peptides of purified rat phospholipase inhibitor protein. As a result of this comparison, we found that the nucleotide sequences of all clones isolated coded for amino acid sequences that had a marked homology to the amino acid sequences of our purified rat phospholipase inhibitor protein. (Compare FIGS. 1 and 2 with FIG. 4.)

The cDNA sequences of this invention can be operatively-linked to expression control sequences and used in various mammalian or other eukaryotic or prokaryotic host cells to produce the human phospholipase inhibitor-like polypeptides coded for by them. In addition, the cDNA sequences of the invention are useful as probes to screen human cDNA libraries for other sequences coding for phospholipase inhibitor-like polypeptides. The cDNA sequences of this invention are also useful as probes to screen human genomic DNA libraries to select human genomic DNA sequences coding for phospholipase inhibitor-like polypeptides. These genomic sequences, like the above cDNA sequences of this invention, are then useful to produce the phospholipase inhibitor-like polypeptides coded for by them. The genomic sequences are particularly useful in transforming mammalian cells to produce human phospholipase inhibitor-like polypeptides.

The human phospholipase inhibitor-like polypeptides produced by the methods of this invention are useful as anti-inflammatory agents and in anti-inflammatory methods and therapies. For example, such compositions may comprise an effective amount of a phospholipase inhibitor-like polypeptide of this invention to reduce inflammation and a pharmaceutically acceptable carrier. Such therapies generally comprise a method of treating patients in a pharmaceutically acceptable manner with those compositions.

METHODS AND MATERIALS

A wide variety of host/cloning vehicle combinations may be employed in cloning or expressing the human phospholipase inhibitor-like polypeptide DNA sequences prepared in accordance with this invention. For example, useful cloning or expression vehicles may consist of segments of chromosomal, non-chromosomal and synthetic DNA sequences, such as various known derivatives of SV40 and known bacterial plasmids, e.g., plasmids from E.coli including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single-stranded DNA phages and vectors derived from combinations of plasmids and phage DNAs such as plasmids which have been modified to employ phage DNA or other expression control sequences or yeast plasmids such as the 2μ plasmid or derivatives thereof.

Within each specific cloning or expression vehicle, various sites may be selected for insertion of the human phospholipase inhibitor-like polypeptide DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences of this invention. These expression control sequences include, for example, the lac system, the β-lactamase system, the trp system, the TAC system, the TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively linked to one or more of the above-described expression control sequences in the expression vector. Such operative linking, which may be effected before or after the chosen human phospholipase inhibitor protein DNA sequence is inserted into a cloning vehicle, enables the expression control sequences to control and promote the expression of the DNA sequence.

The vector or expression vehicle, and in particular the sites chosen therein for insertion of the selected DNA fragment and the expression control sequence employed in this invention is determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular phospholipase inhibitor protein sequence is determined by a balance of these factors, not all selections being equally effective for a given case.

It should also be understood that the DNA sequences coding for the phospholipase inhibitor-like polypeptides of this invention that are inserted at the selected site of a cloning or expression vehicle may include nucleotides which are not part of the actual gene coding for the desired phospholipase inhibitor or may include only a fragment of the entire gene for that protein. It is only required that whatever DNA sequence is employed, a transformed host will produce a phospholipase inhibitor-like polypeptide. For example, the phospholipase inhibitor-related DNA sequences of this invention may be fused in the same reading frame in an expression vector of this invention to at least a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired phospholipase inhibitor-related DNA sequence, improve purification or permit secretion, and preferably maturation, of the phospholipase inhibitor-like polypeptide from the host cell. The phospholipase inhibitor protein-related DNA sequence may alternatively include an ATG start codon, alone or together with other codons, fused directly to the sequence encoding the first amino acid of a mature native phospholipase inhibitor-like polypeptide. Such constructions enable the production of, for example, a methionyl or other peptidyl-phospholipase inhibitor-like polypeptide, that is part of this invention. This N-terminal methionine or peptide may then be cleaved intra- or extra-cellularly by a variety of known processes or the polypeptide used together with the methionine attached to the peptide in the anti-inflammatory compositions and methods of this invention.

The cloning vehicle or expression vector containing the phospholipase inhibitor-like polypeptide coding sequences of this invention is employed in accordance with this invention to transform an appropriate host so as to permit that host to express the phospholipase inhibitor-like polypeptides for which the DNA sequence codes.

Useful cloning or expression hosts may include strains of *E. coli*, such as *E. coli* C600, *E. coli* ED8767, *E. coli* DH1, *E. coli* LE392, *E. coli* HB 101, *E. coli* X1776, *E. coli* X2282, *E. coli* MRCI, and strains of Pseudomonas, Bacillus, and Streptomyces, yeasts and other fungi, animal hosts, such as CHO cells or mouse cells, other animal (including human) hosts, plant cells in culture or other hosts.

The selection of an appropriate host is also controlled by a number of factors recognized by the art. These include, for example, compatibility with the chosen vector, toxicity of proteins encoded by the hybrid plasmid, susceptibility of the desired protein to proteolytic degradation by host cell enzymes, contamination or binding of the protein to be expressed by host cell proteins difficult to remove during purification, ease of recovery of the desired protein, expression characteristics, bio-safety and cost. A balance of these factors must be struck with the understanding that not all host vector combinations may be equally effective for either the cloning or expression of a particular recombinant DNA molecule.

It should be understood that the human phospholipase inhibitor-like polypeptides (prepared in accordance with this invention in those hosts) may include polypeptides in the form of fused proteins (e.g., linked to a prokaryotic, eukaryotic or combination N-terminal segment to direct excretion, improve stability, improve purification or improve possible cleavage of the N-terminal segment), in the form of a precursor of phospholipase inhibitor-like polypeptides (e.g., starting with all or parts of a phospholipase inhibitor-like polypeptide signal sequence or other eukaryotic or prokaryotic signal sequences), in the form of a mature phospholipase inhibitor-like polypeptide, or in the form of an fmet-phospholipase inhibitor-like polypeptide.

One particularly useful form of a polypeptide in accordance with this invention, or at least a precursor thereof, is a mature phospholipase inhibitor-like polypeptide with an easily cleaved amino acid or series of amino acids attached to the amino terminus. Such construction allows synthesis of the protein in an appropriate host, where a start signal that may not be present in the mature phospholipase inhibitor is needed, and then cleavage in vivo or in vitro of the extra amino acids to produce mature phospholipase inhibitor-like polypeptides. Such methods exist in the art. See, e.g., U.S. Pat. Nos. 4,332,892, 4,338,397, and 4,425,437. The polypeptides may also be glycosylated, like some native phospholipase inhibitor proteins, unglycosylated, or have a glycosylation pattern different than that of native phospholipase inhibitor proteins. Such glycosylation will result from the choice of host cell or post-expression treatment chosen for the particular inhibitor.

The polypeptides of the invention also include phospholipase inhibitor-like polypeptides that are coded on expression by DNA sequences characterized by different codons for some or all of the codons of the present DNA sequences. These substituted codons may code for amino acids identical to those coded for by the codons replaced but result in higher yield of the polypeptide. Alternatively, the replacement of one or a combination of codons leading to amino acid replacement or to a longer or shorter phospholipase inhibitor-like polypeptide may alter its properties in a useful way (e.g., increase the stability, increase the solubility or increase the therapeutic activity).

In order that this invention may be better understood, the following examples are set forth. These examples are for purposes of illustration only and are not to be construed as limiting the scope of the invention in any manner.

EXAMPLE

A. Purification of a Rat Phospholipase $A_2$ Inhibitor Protein

We injected male Wistar rats (200–250 kg) subcutaneously with 0.1 ml of the glucocorticoid, dexamethasone phosphate (1.25 mg/kg rat) in 0.9% NaCl to induce production of phospholipase $A_2$ inhibitor protein. We then sacrificed the rats one hour after injection by intracardiac injection with Euthasate and washed the peritoneal cavities with 10 ml of phosphate buffered saline (50 mM KH pH 7.3, 150 mM NaCl containing 2 U/ml heparin and 50 μM phenylmethylsulfonylfluoride). After we cleared the lavages of cells and other particulate matter by centrifugation in an International centrifuge at top speed for 30 min, we assayed the combined supernatants for phospholipase inhibitor protein by measuring the inhibition of release of labeled oleic acid from autoclaved E. coli membranes in the presence of the supernatant and porcine pancreatic phospholipase $A_2$.

We performed this in vitro assay as follows: we mixed 200 μl samples from the peritoneal exudate supernatant in 1.5 ml Eppendorf tubes with 50 μl of 0.7M Tris-HCl (pH 8.0), 60 mM $CaCl_2$ buffer on ice. We then added 50 μl of diluted porcine pancreatic phospholipase $A_2$ (Catalogue no. P9139, Sigma Chemicals) and mixed and incubated the solutions on ice for 1 h. Dilutions of the phospholipase $A_2$ suspension into buffer (70 mM Tris-HCl (pH 8.0), 6 mM $CaCl_2$) containing 2.5 mg/ml bovine serum albumin (BSA) were such that the final concentrations of phospholipase and BSA were 100 ng/50 μl and 25 μg/50 μl, respectively. We then added 25 μl of autoclaved $^3$H-oleic acid-labeled E. coli as substrate and incubated the mixtures at 6° C. for 8 min (both the temperature and length of incubation must be determined for each batch of E. coli utilized).

We prepared the substrate $^3$H-oleic acid-labeled E. coli as follows: We grew an overnight culture of E. coli in tryptone medium (1% bactotryptone, 0.5% NaCl), diluted it 1:20 with fresh broth and monitored cell growth with a Klett meter. At a reading of 40 (i.e., when cells were growing well), we added a 1:100 dilution of Brij 35 (polyoxyethylene-23-ether, Sigma Chemicals, 10% solution in water) and a 1:200 dilution of $^3$H-oleic acid (9,10-$^3$H-[N]-oleic acid, New England Nuclear) at 10 mCi/ml. After 5 h, when cell growth leveled off, we autoclaved the suspension for 20 min at 120° C. and stored the flask overnight at 4° C. We then pelleted the bacteria by centrifugation for 30 min at 16,000 rpm in an SS34 rotor at 4° C. and combined the loose pellets into a singe tube. We washed the bacteria four times, or until counts in the supernatant were low, with suspension buffer (0.7M Tris-HCl (pH 8.0), 10 mM $CaCl_2$) plus 0.1% BSA. We stored the bacteria at 4° C. in suspension buffer containing 0.2% sodium azide. Typically, we prepared a 400 ml culture labeled with 20 mCi of 3H-oleic acid. This yielded about $7 \times 10^8$ cpm or about 10% of the input counts in labeled bacteria. For each point in an assay, we used 100,000 cpm, which was added in a volume of 25 μl. Immediately prior to use, we washed our aliquots first in 200 mM Tris-HCl (pH 8.0), 12 mM EDTA (left on ice 30 min) and then in 25 mM Tris-HCl (pH 8.0).

After the brief incubation of substrate (autoclaved labeled E. coli) with inhibitor plus phospholipase $A_2$, the reaction was stopped immediately by adding 100 μl of 2N HCl to each tube followed by the addition of 100 μl of 20 mg/ml delipidated BSA (99% albumin, Sigma Chemicals). Tubes were vortexed and incubated on ice for 30 min. The latter step was crucial for extracting the lipase digestion products from the particulate membranes.

We then pelleted the E. coli in an Eppendorf centrifuge for 5 min at 10,000 g and counted 250 μl of each supernatant in 4 ml of a scintillation cocktail compatible with aqueous solutions. In this assay, we tested each sample in duplicate using an internal control in which the sample plus E. coli substrate was incubated both in the presence and absence of added phospholipase. This in vitro assay demonstrated that our peritoneal exudates contained phospholipase inhibitory activity.

To purify the phospholipase inhibitor protein from the above-described peritoneal exudate supernatant, we first added additional protease inhibitors to the supernatant. These typically included aprotinin (20 μg/ml), soybean trypsin inhibitor (20 μg/ml) and EGTA (ethyleneglycol-bis(aminoethyl ether) N,N'-tetraacetic acid) (0.5 mM). We incubated the exudate at 37° C. for 1 h in the presence of 0.1 U/ml calf intestinal alkaline phosphatase and concentrated it two-fold by ultrafiltration to a final protein concentration of 5 mg/ml using an Amicon apparatus (PM10 membrane). We next dialyzed the supernatant overnight at 4° C. against 40 volumes of 20 mM Tris-HCl (pH 8.1) and subjected it to DE52 ion exchange column chromatography (Whatman Ltd., column dimensions: 1 cm dia. × 17 cm). Prior to use, we had equilibrated the DE52 resin with 25 mM Tris-HCl (pH 8.1). We collected the flow-through fractions and concentrated them an additional 25-fold by Amicon ultrafiltration (PM10 membrane). We then subjected the concentrate to a gel filtration column (P150 resin) in 25 mM Tris-HCl (column dimensions: 2.5 cm dia. × 40 cm) and monitored the column fractions for protein using absorbance at 280 nm and using the phospholipase inhibitory activity assay described above. We detected peak activity at 35–40,000 molecular weight.

We lyophilized these high activity fractions, dialyzed them against 25 mM Tris-HCl (pH 6.8) containing 0.2% SDS and analyzed them using a preparative SDS-polyacrylamide gel (main gel: 15% acrylamide, 0.8% methylene bisacrylamide; stacking gel: 7.6% acrylamide, 0.21% methylene bisacrylamide). The gel analysis yielded four major protein bands. According to a modification of the Western blotting technique [H. Towbin et al., "Electrophoretic Transfer Of Proteins From Polyacrylamide Gels To Nitrocellulose Sheets", Proc. Natl. Acad. Sci. U.S.A., 76, pp. 4350-54 (1979)] using a horse radish peroxidase antibody conjugate to visualize the immunoreactive species, we found that only one of the four major bands cross reacted with a neutralizing antibody which we prepared against a snake venom phospholipase inhibitory protein. Accordingly, we excised this region of the gel, electroeluted and precipitated the contained protein from it with 20% trichloroacetic acid and pelleted the protein by centrifugation for 20 min at 10,000 g. After washing the pellets twice with 5 ml of −20° C. acetone, each washing being followed by a centrifugation step, we dried the pellets under vacuum.

We then digested the protein either with cyanogen bromide or with trypsin. When utilizing cyanogen bromide digestion, we digested the pellets containing approximately 100 μg protein with 200 mg/ml of cyanogen bromide in the dark for 16 h at 25° C. in 0.5 ml of 70% formic acid. We then diluted the reaction mixture 15-fold with water and lyophilized it. When utilizing tryptic digestion, we first resuspended the pellets in 0.1M NH₄HCO₃ plus 0.1 mM CaCl₂, carboxymethylated the mixture with iodoacetic acid and then incubated it with trypsin for 24 h at 37° C. During this incubation, we added trypsin three times to a final concentration of 1.5% of total protein at time zero, 2.5% after 4 h and 3.5% after 19 h.

We resolved the cleavage fragments from these digestions by high pressure liquid chromatography using a C8 column (Brownlee RP-3) for the cyanogen bromide digestion products and using a C18 column (Spectraphysics) for the tryptic digestion products, utilizing in both cases a gradient of acetonitrile from 0–75% in 0.1% trifluoroacetic acid to elute bound fragments. We then subjected the peak fractions to sequence analysis using a gas phase sequencer (Applied Biosystems 470A). PITH-amino acids were analyzed by high pressure liquid chromatography on a 5 μm cyanocolumn (Hypersil), using a gradient of acetonitrile:methanol (4:1) from 15–55% in 0.02M sodium acetate (pH 5.7).

Figure 1:
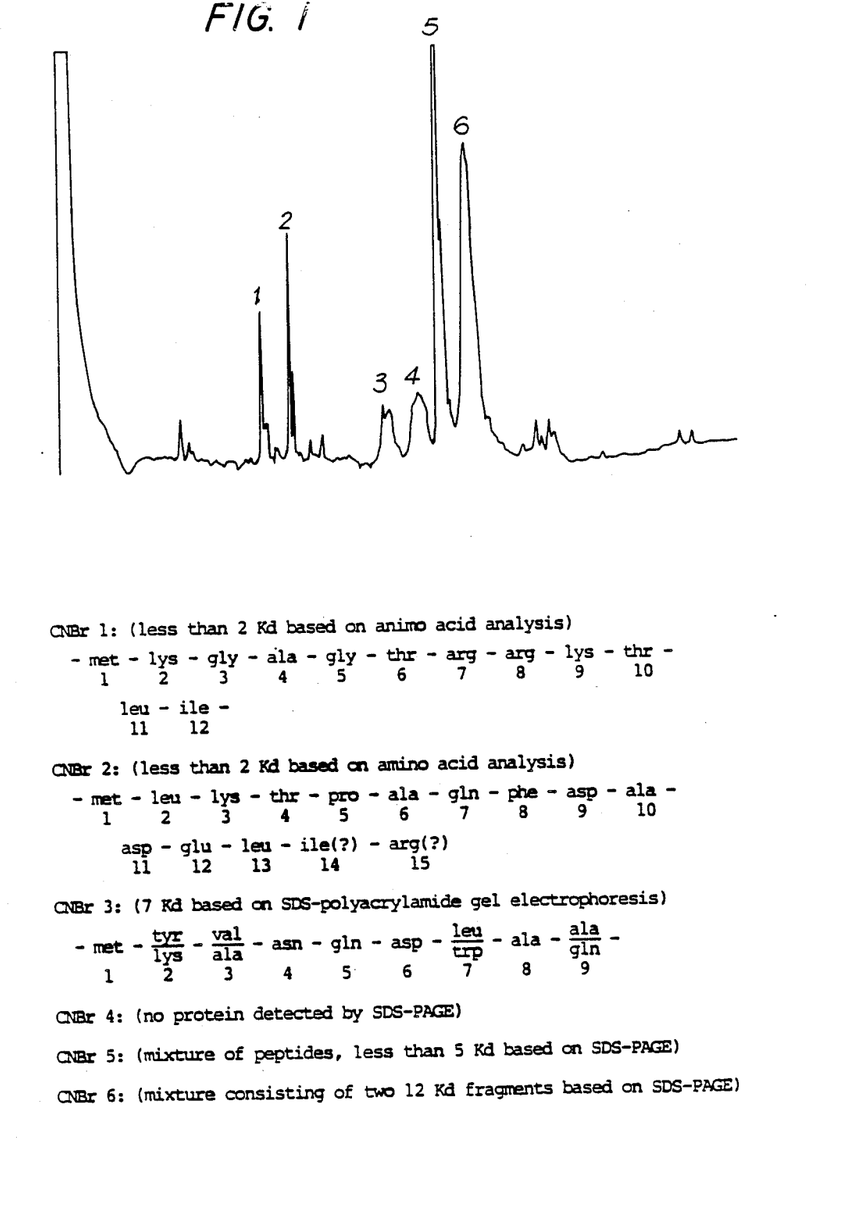
FIG. 1 depicts the amino acid sequences of fragments obtained from a cyanogen bromide digestion of rat phospholipase $A_2$ inhibitor protein.

FIG. 1 shows the amino acid sequences of the fragments produced by cyanogen bromide digestion of our purified rat phospholipase inhibitor protein. Of six major peaks, only three yielded unique sequences (CNBr 1, 2 and 3). These sequences are shown at the bottom of FIG. 1. Of the remaining peaks, two (CNBr 5 and 6) contained mixtures of fragments and thus could not be sequenced, and peak 4 was a column artifact from which no protein was detected.

Figure 2:
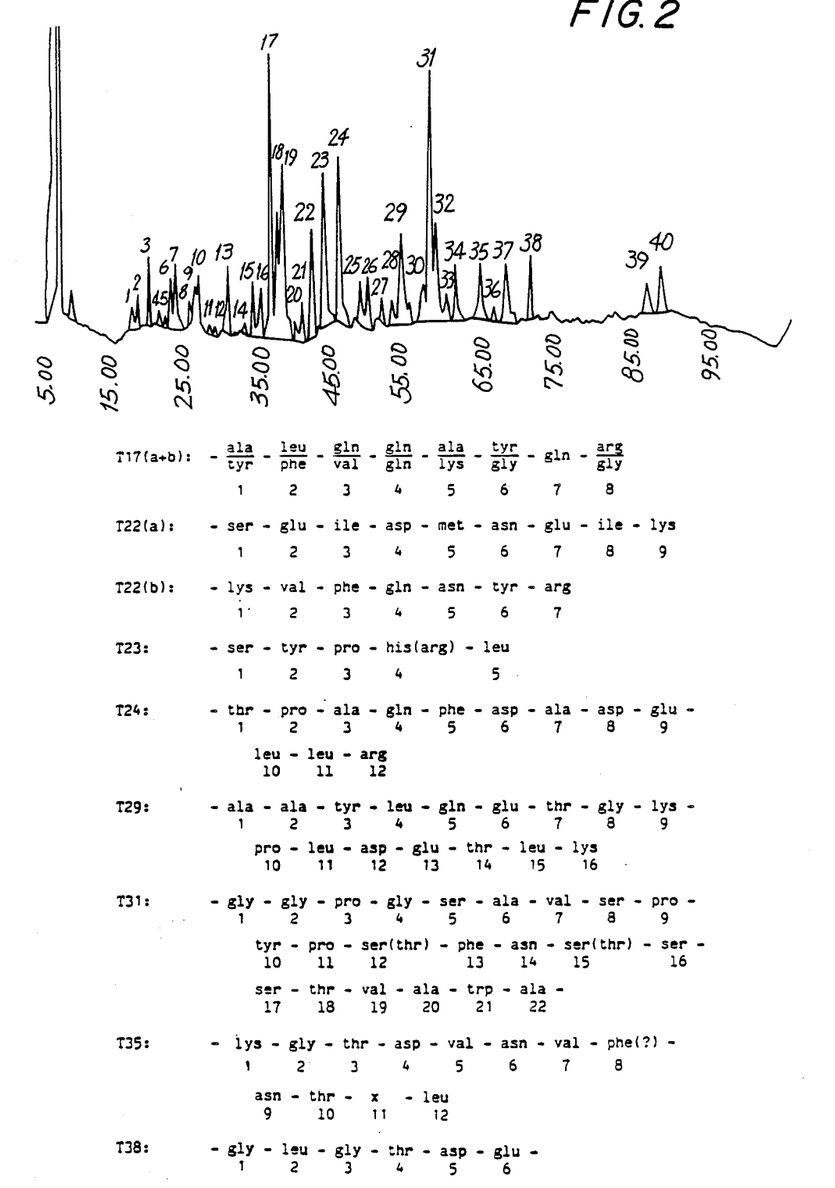
FIG. 2 depicts the amino acid sequences of fragments obtained from tryptic digestion of rat phospholipase $A_2$ inhibitor protein.

FIG. 2 shows the amino acid sequences of fragments from tryptic digestion. Although tryptic digestion produced over forty peaks, the amino acid sequences of only nine fractions are shown in FIG. 2. In instances where peaks contained more than one peptide, the appropriate fractions were subjected to a second chromatography step. T22a and T22b are sequences derived from the two components of peak 22 which were resolved when peak 22 was rechromatographed on the same column but at a neutral pH.

Figure 3:
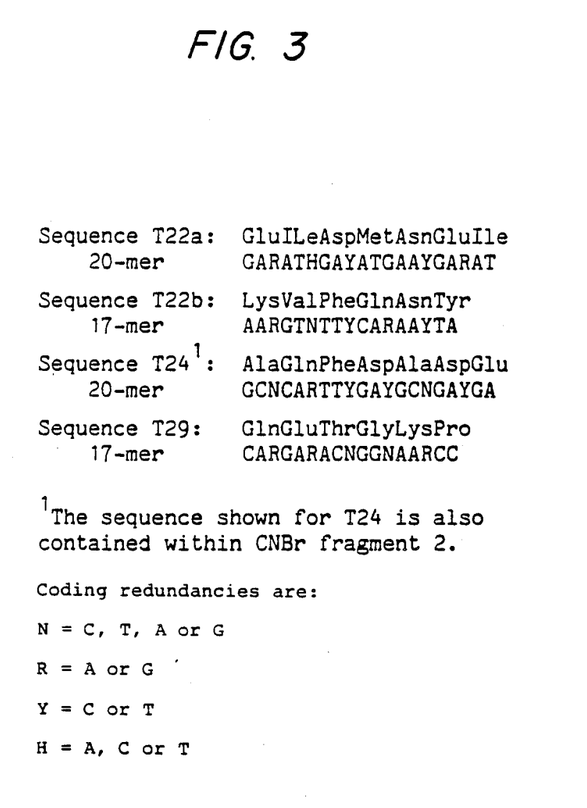
FIG. 3 shows the four pools of chemically synthesized oligonucleotide DNA probes of the invention.

B. Synthesis of Oligonucleotide DNA Probes for Phospholipase Inhibitor Protein Sequences Having determined the amino acid sequences of various regions of a rat phospholipase inhibitor protein (see FIGS. 1 and 2), we chemically synthesized four pools of antisense oligonucleotide DNA probes that coded for some of those protein sequences (see FIG. 3). We decided to synthesize the four pools shown in FIG. 3 because they corresponded to regions of the rat phospholipase inhibitor protein that have minimal nucleic acid degeneracy. For each amino acid sequence, we synthesized mixtures of probes complementary to all possible codons. Furthermore, we synthesized the probes such that they were complementary to the DNA sequences which code for the amino acid sequence, i.e., the probes were antisense, to enable the probes to recognize the corresponding sequences in mRNA as well as in DNA. The amino acid sequences of the four selected regions of the rat phospholipase inhibitor protein and all the possible nucleotide codon combinations that encode them are shown in FIG. 3. Coding degeneracies are indicated as follows: N=C, T, A, or G; R=A or G; Y=C or T; and H=A, C, or T.

Two pools of the probes, derived from sequences in the tryptic fragments T22a and T24 of FIG. 2, are 20-mers with 48 and 256 fold degeneracies, respectively. The other two probe pools are 17-mers with 64 and 128 fold degeneracies. To reduce further the degeneracies in the probes, we also prepared each pool in subpools, e.g., we prepared the 48 fold degenerate 20-mer of T22a in three subpools of 16 and synthesized the other probes in four subpools. The probes in each pool were end-labeled with ³²P using [γ]-³²P-ATP and T4 polynucleotide kinase.

To test if our synthetic probes actually recognized human sequences, we hybridized the four subpools of T24 to GeneScreen filters containing poly (A) mRNA from the human macrophage cell line U-937, which had been induced with 10⁻⁷M PMA[4β-phorbol 12β myristate 13α-acetate] and 10-5 dexamethasone, utilizing the Northern blotting technique [H. Lehrach et al., *Biochemistry*, 10, pp. 4743-51 (1977)]. Subpools 2 and 3 of T24 hybridized to the mRNA and were detected as an 1800 base pair band upon autoradiography.

C. Construction and Screening of a Human cDNA Library

We constructed a human cDNA library from poly (A) mRNA isolated from human macrophage cell line U937. The cDNA sequences were inserted into λgt10 and amplified in *E. coli* C600 hfl cells.

1. EXTRACTION OF RNA FROM HUMAN U937 CELLS

We induced human macrophage U937 cells in culture with dexamethasone (10⁻⁵M) and phorbol ester (10⁻⁷M) and resuspended pellets containing 1.2×10⁹ cells in 48 ml lysis buffer (0.2M Tris-HCl (pH 8.0), 0.1M LiCl, 25 mM EDTA, 1% SDS) plus 5 mM vanadyl complex (Bethesda Research Labs) by vortexing. We used the cells by addition of 24 ml phenol and vortexed for 5 min. We added 24 ml chloroform to the lysis mixture which was then shaken for 10 min. We separated the organic and aqueous phases by centrifugation in a clinical centrifuge at room temperature for 10 min. We reextracted the aqueous phase two times with phenol:-chloroform (1:1), then two times with chloroform only. We next ethanol-precipitated the nucleic acids in 0.3M sodium acetate at −20° C. overnight and pelleted the nucleic acid at 14k rpm in a Sorvall RC2B centrifuge (SS34 rotor) at 4° C. for 20 min. We resuspended the pellets in 5 ml 0.3M sodium acetate, and ethanol-precipitated the nucleic acid again as described above. We resuspended the final pellet in 300 μl H₂O and stored it at −20° C.

This RNA preparation was enriched for poly(A) RNA by passage over an oligo(dT)-cellulose column (PL Biochem).

2. Construction of a U937 cDNA-λgt10 Library
cDNA Synthesis

We synthesized cDNA from 20 μg poly (A)+ mRNA isolated as described above. We diluted the poly (A)+ mRNA to 500 μg/ml in H₂O, heated it to 65° C. for 3 min, quick cooled it in a dry ice-propanol bath and then thawed it. The RNA was then added to a reaction mixture composed of 0.1M Tris-HCl (pH 8.3) at 42° C., 0.01M MgCl₂, 0.01M DTT, 1 mM dCTP, 1 mM dGTP, 1 mM dTTP, 0.5 mM dATP and 100 μCi α-ATP32 (3000 Ci/mmole, Amersham or New England Nuclear), 20 μg oligo (dT)12-18 (PL Biochem), 0.03M β-mercaptoethanol, 5 mM Vanadyl Ribonucleoside Complex (Bethesda Research Labs), 169 U AMV Reverse Transcriptase (Seikagaku America). Final volume of the reaction mixture was 200 μl. We incubated this mixture for 2 min at room temperature and 6 h at 44° C. We terminated the reaction by addition of 1/10 vol 0.5M Na₂EDTA (pH 8.0).

We adjusted the reaction mixture to 0.15M NaOH and incubated the mixture at 37° C. for 12 h followed by neutralization with 1/10 vol 1M Tris-HC (pH 8.0) and HCl. This was extracted with phenol:chloroform saturated TE buffer (10 mM Tris-HCl (pH 7.0) and 1 mM Na2EDTA). The aqueous phase was chromatographed through a 5 ml sterile plastic pipet containing a 7×29 cm bed of Sephadex G150 in 0.01M (pH 7.4), 0.4M NaCl, 0.01M Na2EDTA, 0.05% SDS. We pooled the front peak minus tail and precipitated the cDNA with 2.5 vol 95% ethanol at −20° C. This reaction yielded 1 μg of single-stranded cDNA.

Double Strand Synthesis

We resuspended the single-stranded cDNA in 200 μl (final vol) 0.1M Hepes (pH 6.9), 0.01M MgCl, 0.0025M DTT, 0.07M KCl, 1 mM dXTPs and 75 U Klenow fragment DNA polymerase (Boehringer-Mannheim) and incubated the reaction mixture at 14° C. for 21 h. Reaction was terminated by addition of Na EDTA (pH 8.0) to 0.0125M, extracted with phenol:chloroform, as in the first cDNA step, and the aqueous phase was chromatographed on a G150 column in 0.01M Tris-HCl (pH 7.4), 0.1M NaCl, 0.01M Na2EDTA, 0.05% SDS. We again pooled the radioactive peak minus the tail and ethanol-precipitated the DNA.

We then incubated the DNA obtained with 42 U reverse transcriptase in 50 μl 0.1M Tris-HCl (pH 8.3), 0.01M MgCl2, 0.01M DDT, 0.1M KCl, 1 mM dXTPS, 0.03M β-mercaptoethanol for 1 h at 37° C. to complete double-strand synthesis. The reaction was terminated and processed as described above.

We cleaved the hairpin loop formed during double strand synthesis as follows: We redissolved the pellet in 50 μl 0.03M sodium acetate (pH 4.5), NaCl, 0.003M ZnCl2 and treated it with 100 0.3M U S1 nuclease (Sigma) for 30 min at room temperature. Reaction was terminated by addition of EDTA and processed as described above. The yield after S1 treatment was 900 ng dsDNA.

To assure blunt ends following S1 nuclease digestion, we treated the DNA with Klenow in 0.01M Tris-HCl (pH 7.4), 0.01M MgCl2, 1 mM DTT, 0.05M NaCl, 80 μM dXTP and 12.5 U Klenow in 60 μl for 90 min at 14° C., extracted with 50:50 phenol:chloroform, and chromatographed the DNA on a G50 spin column (1 ml syringe) in 0.01M Tris-HC (pH 7.4), 0.1M NaCl, 0.01M EDTA, 0.05% SDS.

We next methylated the dsDNA by treating the DNA with EcoRI methylase in 30 μl final vol 0.1M Tris-HCl (pH 8.0), 0.01M Na2EDTA, 24 μg BSA, 0.005M DTT, 30 μM S-adenosylmethionine and 5 U EcoRI Methylase for 20 min at 37° C. The reaction was heated to 70° C. for 10 min, cooled, extracted with 0:50 pheno:chloroform and chromatographed on a G50 spin column as described above.

We ligated the 900 ng cDNA to phosphorylated EcoRI linkers (New England Biolabs) using the following conditions: 0.05M Tris-HCl (pH 7.8), 0.01M MgCl2, 0.02M DTT, 1 mM ATP, 50 μg/ml BSA, 0.5 μg linker, 300 U T4 DNA ligase in 7.5 μl final volume for 32 h at 14° C.

We adjusted the reaction to 0.1M Tris-HCl (pH 7.5), 0.05M NaCl, 5 mM MgCl2, 100 μg/ml BSA, 125 U EcoRI (New England Biolabs), incubated the mixture for 2 h at 37° C., extracted with 50:50 phenol:chloroform and chromatographed the DNA on a G50 spin column as described earlier.

We redissolved cDNA in 100 μl 0.01M Tris-HCl (pH 7.5), 0.1M NaCl, 1 mM EDTA and chromatographed it on a 1×50 cm Biogel A50 (BIORAD) column which had been extensively washed in the same buffer (to remove ligation inhibitors). Aliquots of fractions were run on a 1% agarose gel in TBE buffer (0.089M Tris-HCl, 0.089M boric acid and 2.5 mM Na EDTA), dried and exposed at −70° C. overnight. We pooled all fractions that were larger than 500 base pairs and ethanol-precipitated the DNA for cloning into an EcoRI-cut λgt10 cloning vector. The size fractionation column yielded 126 ng of cDNA, average size approximately 1500 bp.

Library Construction

We incubated 5 μg EcoRI-cut λgt10 with 0 ng cDNA and T4 DNA ligase buffer at 42° C. for 15 min to anneal cos sites, followed by centrifugation for 5 sec in an Eppendorf centrifuge and addition of ATP to 1 mM and 2400 U T4 DNA ligase (New England Biolabs) in a final vol of 50 μl. [See Huynh, Young and Davis, "Constructing And Screening cDNA Libraries in λgt10 And λgt11", in *DNA Cloning: A Practical Approach* (D. Glover, ed.), IRL Press (Oxford 1984)]. The ligation was incubated at 14° C. overnight. We packaged the λgt10 cDNA ligation mixture into phage particles using an Amersham packaging mix [Amersham packaging protocol] and diluted with 0.5 ml SM buffer (100 mM NaCl, 10 mM MgSO4, 50 mM Tris-HCl (pH 7.5) and 0.01% gelatin).

We next infected *E. coli* C600 hfl cells with these phage particles to form a cDNA library of 1 x $10^7$ independent recombinants [See T. Maniatis, et al., *Molecular Cloning*, p. 235 (Cold Spring Harbor 1982)].

For plating and amplification of the library, 1 ml of cells plus 250 μl packaging mix was incubated at room temperature for 15 min, diluted to 50 ml in LB plus MgSO4 top agarose at 50° C. and plated on LB Mg Nunc plates. This represented a plaque density of $2 \times 10^5$ plate. The plates were incubated at 37° C. for approximately 8 h until plaques were nearly touching.

We flooded the plates with 50 ml of cold SM buffer (0.01M Tris-HCl (pH 7.5), 0.01M MgCl2, 0.1 mM Na2EDTA) and eluted on a gyro-rotary shaker overnight at 4° C. We pooled the eluants into 250 ml bottles and spun at 6K for 10 min in a Sorval GSA rotor. We treated the supernatants with an equal volume of cold 20% PEG 4000- 2M NaCl in ice for 3 h and pelleted the phages by centrifugation at 4K for 30 min in an H4000 rotor in an RC-3B Sorvall centrifuge. The phage pellets were thoroughly drained, resuspended in 60 ml SM, and spun at 10,000 rpm in a SS34 rotor to remove debris. The supernatants were adjusted to 3.5M CsCl by addition of 7 g CsCl to 10 ml supernatant. We obtained phage bands by centrifugation in a 70.1 Beckman rotor at 50,000 rpm for 18 h at 15° C. We pooled the phage bands and stored them at 4° C. for library stock. The titer obtained was $2.2 \times 10^{13}$ PFU/ml.

Screening Of The Library

We screened the library with our labeled oligonucleotide probes, pools 2 and 3, for phospholipase inhibitor protein sequences using the plaque hydridization screening technique of Woo [S. L. C. Woo, "A Sensitive And Rapid Method For Recombinant Phage Screening", in *Methods In Etymology*, 8, pp. 389-96 (Academic Press 1979)].

An overnight culture of C600 hfl cells in L broth and 0.2% maltose was pelleted and resuspended in an equal volume of SM buffer. We pre-adsorbed 0.9 ml of cells with $2 \times 10^5$ phage particles at room temperature for 15 min. We diluted the suspension to 50 ml in LB plus 10 mM MgSO4 and 0.7% agarose at 55° C. and plated it on LB Mg Nunc plates. We screened 10 such plates. We incubated the plates at 37° C. for approximately 8 h until plaques were nearly touching. We then chilled the plates at 4° C. for 1 h to allow the agarose to harden. We presoaked GeneScreen Plus filters in a 1:10 dilution of the overnight *E. coli* C600 hfl cells for 10 min at room temperature so that a lawn of *E. coli* cells covered each filter. We then transferred the λ phage particles from the plaque library plates to these bacteria-coated filters as follows:

We placed the filters onto the plates containing the recombinant plaques for 5 min, and then lifted and incubated the filters with the phage-containing side up on LB +10 mM MgSO plates at 37° C. for 5 h.

These filters were then lysed by placing them onto a pool of 0.5N NaOH for 5 min, then neutralized on 1M Tris-HCl (pH 7.0), submerged into M Tris-HCl (pH 7.0) and scrubbed clean of cell debris.

We prehybridized and hybridized the filters to the oligonucleotide probes 2 and 3 in 0.2% poly-vinyl-pyrolidone (M.W. 40,000), 0.2% ficoll (M.W. 40,000), 0.2% bovine serum albumin, 0.05M Tris-HCl (pH 7.5), 1M sodium chloride, 0.1% sodium pyrophosphate, 1% SDS, 10% dextran sulfate (M.W. 500,000) and denatured salmon sperm DNA (>100 μg/ml) (according to manufacturer's specifications (New England Nuclear) for plaque screen membranes). We detected hybridizing λ-cDNA sequences by autoradiography.

By means of this technique, we picked 20 positive plaques and rescreened at lower density using the same probes.

We isolated the DNA of these clones, digested with EcoRI, and hybridized them with the four pools of rat phospholipase inhibitor protein probes using the Southern blot technique [E. M. Southern, "Detection Of Specific Sequences Among DNA Fragments Separated By Gel Electrophoresis", *J. Mol. Biol.*, 98, pp. 503–18 (1975)]. Two of the clones, λ9-111 and λ4-211, contained inserted cDNA which hybridized not only to the T24 probe but to the T22*a* and T29 probes as well.

We restricted the DNAs of these phages with EcoRI and isolated the cDNA inserts. By restricting Clone 9-111 with EcoRI we obtained a 400 base pair fragment while restriction of Clone 4-211 gave three EcoRI fragments, 1300, 300 and 75 base pairs in length. We subcloned some of these fragments into plasmid pUC13 to produce recombinant plasmids pL9/20 (9-111), pL4/10 large (4-211, 1300 bp), and pL4/10 small (4-211, 300 bp). We then sequenced these plasmids by the method of Maxam and Gilbert [A. M. Maxam and W. Gilbert, "A New Method For Sequencing DNA", *Proc. Natl. Acad. Sci. U.S.A.*, 74, pp 560–64 (1977)]. This sequencing analysis demonstrated that the clones contained nucleotide sequences which corresponded to the amino acid sequences of the purified rat phospholipase inhibitor protein but seemed to be lacking the most 5' sequence.

A 480 base pair EcoRI-BglII fragment of pL9/20 was used as a probe to rescreen the U937-λgt10 library. 72 positives were isolated and partially plaque purified by rescreening at lower density. The DNA of each of these positives was digested with HhaI and analyzed by the Southern blotting technique [E. M. Southern, supra] using a 30 oligonucleotide sequence (ipo 16) as a probe. Lipo 16 corresponds to the sequence starting at base pair 81-111 of the sequence presented in FIG. 4. 14 of these clones showed a positive signal and were further analyzed by genomic sequencing [G. Church and W. Gilbert, *Proc. Natl. Acad. Sci. U.S.A.*, 81, p. 1991 (1984)] by digesting DNA with MspI and using lipo 16 as probe. Seven clones, λL110, λL106, λL112, λLC, λLH, λIN, and λLDD, contained an 81 base pair sequence 5' to the lipo 16 probe sequence.

Figure 4:
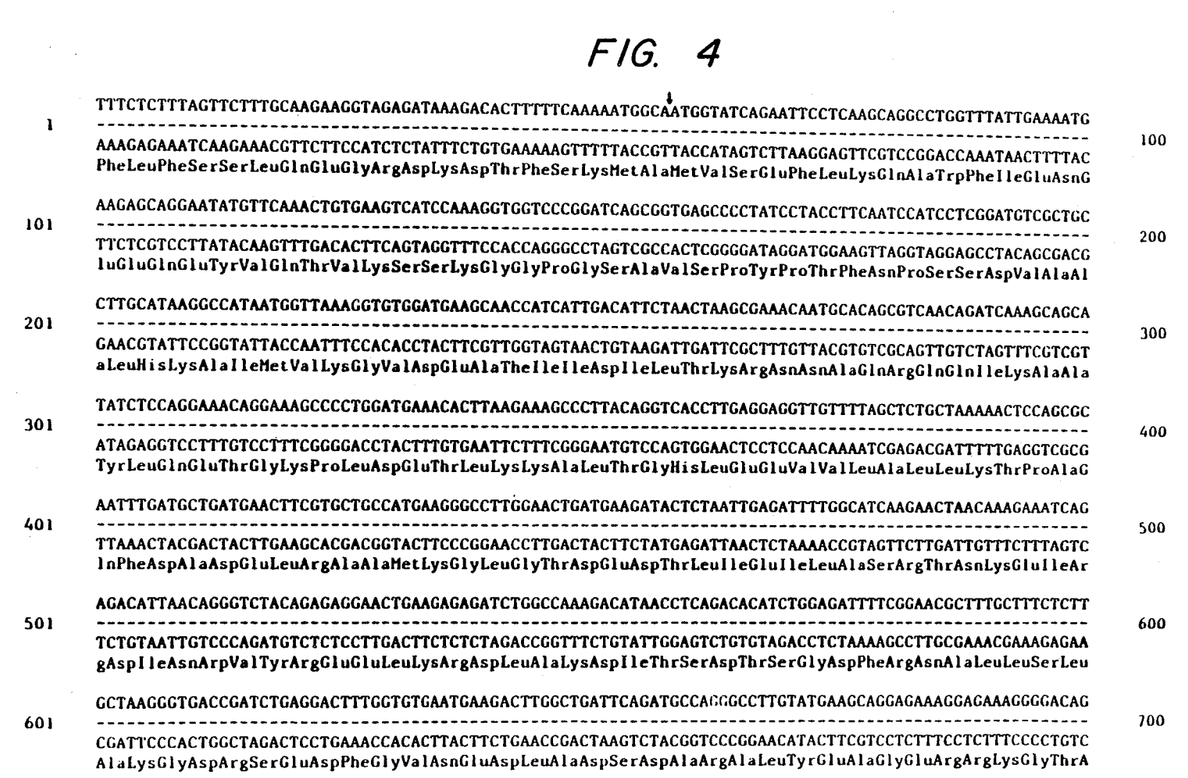
FIG. 4 displays the nucleotide sequence of the cDNA insert of λLC.

These clones contain cDNA sequences having an uninterrupted open reading frame that can code for 363 amino acids (see FIG. 4). We believe that the initiating ATG codon for phospholipase inhibitor protein may be the ATG located at nucleotides 52–55 of FIG. 4. However, the DNA sequence of our clone, reported in FIG. 4, may be lacking one or more codons coding for amino acids in the N-terminal end of native phospholipase inhibitor protein. These potential missing codons may be isolated, if necessary, by one of skill in the art using conventional hybridization conditions from our libraries, or other libraries, of genomic DNA and cDNA using as probes our clones, or more preferably portions of the 5' terminal end of those clones. Full length clones may then be prepared using conventional ligation techniques and our phospholipase inhibitor protein coding clones.

It should also be understood that our cDNA sequence (FIG. 4) may contain part of a putative signal sequence of phospholipase inhibitor protein. The existence of the 3' terminal end of such putative signal sequence may be determined by purifying human phospholipase inhibitor protein, substantially as described above for the corresponding rat protein, and sequencing its amino terminal end. Again, the complete putative signal sequence, if it exists and is preferable for some expression constructions, may be isolated using the techniques described above.

The cDNA sequences of this invention can be further utilized to screen human genomic cosmid or phage libraries to isolate human genomic sequences encoding human phospholipase inhibitor-like polypeptides.*

* For example, an EcoRI fragment of plasmid pL9/20 was used to screen a partial HaeIII-AluI human liver library (R. Lawn et al., "The Isolation And Characterization of Linked Δ and β Globin Genes From A Cloned Library of Human DNA", *Cell*, 15, pp. 1157-74 (1978) and positive clones were obtained.

These human cDNA and genomic sequences can be used to transform eukaryotic and prokaryotic host cells by techniques well known in the art to produce human phospholipase inhibitor-like polypeptides in clinically and commercially useful amounts.

D. Expression of a Phospholipase Inhibitor-Like Polypeptide in *E. coli*

Figure 5:
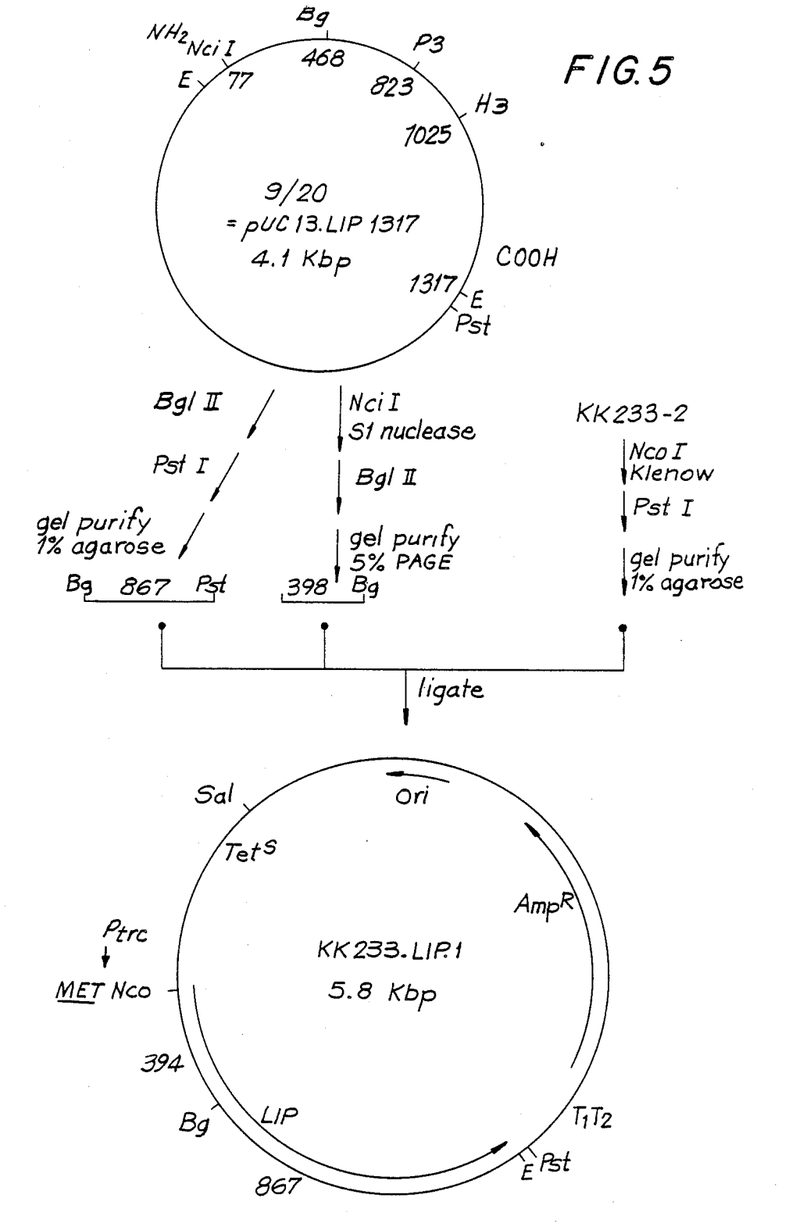
FIG. 5 depicts in schematic outline the construction of plasmid pKK233.LIP.1 used to express in one embodiment the DNA sequences of the invention.

Plasmid pKK233.LIP.1 was constructed by a three part ligation using NcoI-PstI-cut pKK233-2 [E. Amann et al., "Vectors Bearing A Hybrid Trp-Lac Promoter Useful For Regulated Expression Of Cloned Genes In *Escherichia coli*", *Gene*, 25, pp. 167–78 (1983)] and the BglII-PstI and NciI-BglII fragments from pL9/20 (see FIG. 5). Plasmid pL9/20 contains the DNA sequence of nucleotides 67–1376 of the cDNA insert of λLC shown in FIG. 4.

Transformants resulting from this ligation and subsequent transformation into *E. coli* strain HB101 IQ were picked into microtiter wells containing L broth plus ampicillin and grown overnight. The overnight cultures were then replicated onto nitrocellulose filter circles on L broth agar plus ampicillin plates in quadruplicate and incubated for approximately 4 h at 37° C. The nitrocellulose filters were then transferred to L broth plates containing IPTG (10 μg/m) and incubated for 0, 30, 60, or 120 min, followed by lysozyme-detergent treatment to lyse the colonies and finally by Western blot analysis with a cross reactive antiserum that was prepared against the rat phospholipase inhibitor protein. Transformants were also analyzed by plasmid restriction mapping. All the Western positive colonies contained plasmids carrying the predicted restriction fragments. Preparations of *E. coli* from the positive colonies were also analyzed by SDS polyacrylamide gel electrophoresis. With Western blot analysis of these preparations using the antibody against rat phospholipase inhibitor protein, we detected a 31,000 molecular weight truncated protein.

Recombinant DNA sequences prepared by the processes described herein are exemplified by a culture deposited in the culture collection of In Vitro International, Inc., Ann Arbor, Mich. The culture was deposited on Jan. 9, 1985 and is identified as follows: λLC: Accession No. IVI 10042.

IMPROVING THE YIELD AND ACTIVITY OF HUMAN PHOSPHOLIPASE INHIBITOR-LIKE POLYPEPTIDES PRODUCED IN ACCORDANCE WITH THIS INVENTION

The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide sequences normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific phospholipase inhibitor protein coding sequences of this invention from their adjacent nucleotide sequences and to fuse them instead to other known expression control sequences so as to favor higher levels of expression and production of human phospholipase inhibitor-like polypeptides. This having been achieved, the newly engineered DNA fragments may be inserted into higher copy number plasmids or bacteriophage derivatives in order to increase the number of gene copies within the cell and thereby further to improve the yield of expressed phospholipase inhibitor-like polypeptides.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phage λ($O_L P_L$ as described above an $O_R P_R$), a control region of filamentous single-stranded DNA phages, the TAC or TRC system, the promoter for 3-phosphoglycerate kinese or other glycolytic enzymes, the promoters of acid phosphatase, e.g., Pho5, the promoters of the yeast α-mating factors, promoters for mammalian cells such as the SV40 early and late promoters, adenovirus late promoter and metallothionine promoter, and other sequences which control the expression of genes of prokaryotic or eukaryotic cells and their viruses or combinations thereof.

Therefore, to improve the production of the phospholipase inhibitor-like polypeptides of this invention the DNA sequences for that polypeptide may be prepared as before and inserted into a recombinant DNA molecule closer to its former expression control sequence or under the control of one of the above improved expression control sequences. Such methods are known in the art.

Other methods to improve the efficiency of translation involve the insertion of chemically or enzymatically prepared oligonucleotides in front of the initiating codon of the phospholipase inhibitor protein-related DNA sequences of this invention or the replacement of codons at the N-terminal end of the DNA sequence with those chemically or enzymatically prepared oligonucleotides. By this procedure a more optimal primary and higher order structure of the messenger RNA can be obtained. More specifically, a sequence can be so designed that the initiating AUG codon occurs in a readily accessible position (i.e., not masked by secondary structure) either at the top of a hairpin or in other single-stranded regions. Also the position and sequence of the aforementioned Shine-Dalgarno segment can likewise be optimized. The importance of the general structure (folding) of the messenger RNA has been documented [D. Iserentant and W. Fiers "Secondary Structure Of mRNA And Efficiency Of Translation Initiation", *Gene*, 9, pp. 1-12 (1980)].

Further increases in the cellular yield of the phospholipase inhibitor-like polypeptides of this invention may be achieved by increasing the number of genes that can be utilized in the cell. This may be achieved by insertion of the phospholipase inhibitor protein gene (with or without its transcription and translation control elements) in a higher copy number plasmid or in a temperature-controlled copy number plasmid (i.e., a plasmid which carries a mutation such that the copy number of the plasmid increases after shifting the temperature [B. Uhlin et al., "Plasmids With Temperature-Dependent Copy Number For Amplification Of Cloned Genes And Their Products", *Gene*, 6, pp. 91-106 (1979).

Alternatively, an increase in gene dosage can be achieved for example by insertion of recombinant DNA molecules engineered in the way described previously into the temperate bacteriophage λ, most simply by digestion of the plasmid with a restriction enzyme, to give a linear molecule which is then mixed with a restricted phage λ cloning vehicle [e.g., of the type described by N. E. Murray et al., "Lambdoid Phages That Simplify The Recovery Of In Vitro Recombinants", *Mol. Gen. Genet.*, 150, pp. 53-61 (1977) and N. E. Murray et al., "Molecular Cloning Of The DNA Ligase Gene From Bacteriophage T4", *J. Mol. Biol.*, 132, pp. 493-505 (1979)] and the recombinant DNA molecule produced by incubation with DNA ligase. The desired recombinant phage is then selected and used to lysogenize a host strain of *E. coli*.

Therefore, it should be understood that the phospholipase inhibitor-like polypeptide coding sequences of this invention may be removed from the disclosed vectors and inserted into other expression vectors, as previously described (supra) and these vectors employed in various hosts, as previously described (supra) to improve the production of the human phospholipase inhibitor-like polypeptides of this invention.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A recombinant DNA molecule comprising a DNA sequence coding for a phospholipase inhibitor polypeptide and being selected from the group consisting of:
   (a) the cDNA insert of ALC,
   (b) DNA sequences which hybridize to the cDNA insert of ALC and which code on expression for a phospholopase inhibitor, and
   (c) DNA sequences which are degenerate as a result of the genetic code to either of the foregoing DNA sequences and which code on expression for a phospholipase inhibitor.

2. A recombinant DNA molecule according to claim 1, wherein the DNA sequence is selected from the group consisting of:

3. The recombinant DNA molecule according to claim 1 or 2, wherein said DNA sequence is operatively linked to an expression control sequence in the molecule.

4. The recombinant DNA molecule according to claim 3, wherein said expression control sequence is selected from the group consisting of the lac system, the β-lactamase system, a trp system, a trc system, major operator and promoter regions of phage λ, the control region of fd coat protein, the promoter for 3-phosphoglycerate kinase or other glycolytic enzymes, the promoters of acid phosphatase, the promoter of yeast α-mating factors, the SV40 early and late promoter, the adenovirus late promoter and the metallothionine promoter and other sequences which control the expression of genes of prokaryotic or eukaryotic cells and their viruses.

5. The recombinant DNA molecule ALC.

6. A unicellular host transformed with at least one recombinant DNA molecule according to claim 3.

7. The transformed host of claim 6 selected from the group consisting of strains of *E. coli*, Pseudomonas, Bacillus, Streptomyces, yeast, other fungi, mouse or other animal hosts, plant hosts, and human tissue cells.

8. A DNA sequence selected from the group consisting of:

```
TTTCTCTTTAGTTCTTTGCAAGAAGGTAGAGATAAAGACACTTTTTCAAAAAT
GGCAATGGTATCAGAATTCCTCAAGCAGGCCTGGTTTATTGAAAATGAAGAGC
AGGAATATGTTCAAACTGTGAAGTCATCCAAAGGTGGTCCCGGATCAGCGGTG
AGCCCCTATCCTACCTTCAATCCATCCTCGGATGTCGCTGCCTTGCATAAGGC
CATAATGGTTAAAGGTGTGGATGAAGCAACCATCATTGACATTCTAACTAAGC
GAAACAATGCACAGCGTCAACAGATCAAAGCAGCATATCTCCAGGAAACAGGA
AAGCCCCTGGATGAAACACTTAAGAAAGCCCTTACAGGTCACCTTGAGGAGGT
TGTTTTAGCTCTGCTAAAAACTCCAGCGCAATTTGATGCTGATGAACTTCGTG
CTGCCATGAAGGGCCTTGGAACTGATGAAGATACTCTAATTGAGATTTTGGCA
TCAAGAACTAACAAAGAAATCAGAGACATTAACAGGGTCTACAGAGAGGAACT
GAAGAGAGATCTGGCCAAAGACATAACCTCAGACACATCTGGAGATTTTCGGA
ACGCTTTGCTTTCTCTTGCTAAGGGTGACCGATCTGAGGACTTTGGTGTGAAT
GAAGACTTGGCTGATTCAGATGCCAGGGCCTTGTATGAAGCAGGAGAAAGGAG
AAAGGGGACAGACGTAAACGTGTTCAATACCATCCTTACCACCAGAAGCTATC
CACAACTTCGCAGAGTGTTTCAGAAATACACCAAGTACAGTAAGCATGACATG
AACAAAGTTCTGGACCTGGAGTTGAAAGGTGACATTGAGAAATGCCTCACAGC
TATCGTGAAGTGCGCCACAAGCAAACCAGCTTTCTTTGCAGAGAAGCTTCATC
AAGCCATGAAAGGTGTTGGAACTCGCCATAAGGCATTGATCAGGATTATGGTT
TCCCGTTCTGAAATTGACATGAATGATATCAAAGCATTCTATCAGAAGATGTA
TGGTATCTCCGTTTGCCAAGCCCATCCTGGATGAAACCAAAGGAGATTATGAGA
AAATCCTGGTGGCTCTTTGTGGAGGAAACTAAACATTCCCTTGATGGTCTCAA
GCTATGATCAGAAGACTTTAATTATATATTTTCATCCTATAAGCTTAAATAGG
AAAGTTTCTTCAACAGGATTACAGTGTAGCTACCTACATGCTGAAAAATATAG
CCTTTAAATCATTTTTATATTATAACTCTGTATAATAGAGATAAGTCCATTTT
TTAAAAATGTTTTCCCCAAACCATAAAACCCTATACAAGTTGTTCTAGTAACA
ATACATGAGAAAGATGTCTATGTAGCTGAAAATAAAATGACGTCACAAGAC and
ATGGCAATGGTATCAGAATTCCTCAAGCAGGCCTGGTTTATTGAAAATGAAGA
GCAGGAATATGTTCAAACTGTGAAGTCATCCAAAGGTGGTCCCGGATCAGCGG
TGAGCCCCTATCCTACCTTCAATCCATCCTCGGATGTCGCTGCCTTGCATAAG
GCCATAATGGTTAAAGGTGTGGATGAAGCAACCATCATTGACATTCTAACTAA
GCGAAACAATGCACAGCGTCAACAGATCAAAGCAGCATATCTCCAGGAAACAG
GAAAGCCCCTGGATGAACACTTAAGAAAGCCCTTACAGGTCACCTTGAGGAG
GTTGTTTTAGCTCTGCTAAAAACTCCAGCGCAATTTGATGCTGATGAACTTCG
TGCTGCCATGAAGGGCCTTGGAACTGATGAAGATACTCTAATTGGGATTTTGG
CATCAAGAACTAACAAAGAAATCAGAGACATTAACAGGGTCTACAGAGAGGAA
CTGAAGAGAGATCTGGCCATAGACATAACCTCAGACACATCTGGAGATTTTCG
GAACGCTTTGCTTTCTCTTACTAAGGGTGACCGATCTGAGGACTTTGGTGTGA
ATGAGACTTGGCTGATTCAGATGCCAGGGCCTTGTATGAAGCAGGAGAAAGG
AGAAAGGGGACAGACGTAAACGTGTTCAATACCATCCTTACCACCAGAAGCTA
TCCACAACTTCGCAGAGTGTTTCAGAAATACACCAAGTACAGTAAGCATGACA
TGAACAAAGTTCTGGACCTGGAGTTGAAAGGTGACATTGAGAAATGCCTCACA
GCTATCGTGAAGTGCGCCACAAGCAAACCAGCTTTCTTTGCAGAGAAGCTTCA
TCAAGCCATGAAAGGTGTTGGAACTCGCCATAAGGCATTGATCAGGATTATGG
TTTCCCGTTCTGAAATTGACATGAATGATATCAAAGCATTCTATCAGAAGATG
TATGGTATCTCCCTTTGCCAAGCCATCCTGGATGAAACCAAAGGAGATTATGA
GAAAATCCTGGTGGCTCTTTGTGGAGGAAACTAAACATTCCCTTGATGGTCTC
AAGCTATGATCAGAAGACTTTAATTATATATTTTCATCCTATAAGCTTAAATA
GGAAAGTTTCTTCAACAGGATTACAGTGTAGCTACCTACATGCTGAAAAATAT
AGCCTTTAAATCATTTTTATATTATAACTCTGTATAATAGAGATAAGTCCATT
TTTTAAAAATGTTTTCCCCAAACCATAAAACCCTATACAAGTTGTTCTAGTAA
CAATACATGAGAAAGATGTCTATGTAGCTGAAAATAAAATGACGTCACAAGAC.
```

```
TTTCTCTTTAGTTCTTTGCAAGAAGGTAGAGATAAAGACACTTTTTCAAAAAT
GGCAATGGTATCAGAATTCCTCAAGCAGGCCTGGTTTATTGAAAATGAAGAGC
AGGAATATGTTCAAACTGTGAAGTCATCCAAAGGTGGTCCCGGATCAGCGGTG
AGCCCCTATCCTACCTTCAATCCATCCTCGGATGTCGCTGCCTTGCATAAGGC
CATAATGGTTAAAGGTGTGGATGAAGCAACCATCATTGACATTCTAACTAAGC
GAAACAATGCACAGCGTCAACAGATCAAAGCAGCATATCTCCAGGAAACAGGA
AAGCCCCTGGATGAAACACTTAAGAAAGCCCTTACAGGTCACCTTGAGGAGGT
TGTTTTAGCTCTGCTAAAAACTCCAGCGCAATTTGATGCTGATGAACTTCGTG
CTGCCATGAAGGGCCTTGGAACTGATGAAGATACTCTAATTGAGATTTTGGCA
TCAAGAACTAACAAAGAAATCAGAGACATTAACAGGGTCTACAGAGAGGAACT
GAAGAGAGATCTGGCCAAAGACATAACCTCAGACACATCTGGAGATTTTCGGA
ACGCTTTGCTTTCTCTTGCTAAGGGTGACCGATCTGAGGACTTTGGTGTGAAT
GAAGACTTGGCTGATTCAGATGCCAGGGCCTTGTATGAAGCAGGAGAAAGGAG
AAAGGGGACAGACGTAAACGTGTTCAATACCATCCTTACCACCAGAAGCTATC
CACAACTTCGCAGAGTGTTTCAGAAATACACCAAGTACAGTAAGCATGACATG
AACAAAGTTCTGGACCTGGAGTTGAAAGGTGACATTGAGAAATGCCTCACAGC
TATCGTGAAGTGCGCCACAAGCAAACCAGCTTTCTTTGCAGAGAAGCTTCATC
AAGCCATGAAAGGTGTTGGAACTCGCCATAAGGCATTGATCAGGATTATGGTT
TCCCGTTCTGAAATTGACATGAATGATATCAAAGCATTCTATCAGAAGATGTA
TGGTATCTCCGTTTGCCAAGCCCATCCTGGATGAAACCAAAGGAGATTATGAGA
AATCCTGGTGGCTCTTTGTGGAGGAAACTAAACATTCCCTTGATGGTCTCAA
GCTATGATCAGAAGACTTTAATTATATATTTTCATCCTATAAGCTTAAATAGG
AAAGTTTCTTCAACAGGATTACAGTGTAGCTACCTACATGCTGAAAAATATAG
CCTTTAAATCATTTTTATATTATAACTCTGTATAATAGAGATAAGTCCATTTT
TTAAAAATGTTTTCCCCAAACCATAAAACCCTATACAAGTTGTTCTAGTAACA
ATACATGAGAAAGATGTCTATGTAGCTGAAAATAAAATGACGTCACAAGAC and
ATGGCAATGGTATCAGAATTCCTCAAGCAGGCCTGGTTTATTGAAAATGAAGA
GCAGGAATATGTTCAAACTGTGAAGTCATCCAAAGGTGGTCCCGGATCAGCGG
TGAGCCCCTATCCTACCTTCAATCCATCCTCGGATGTCGCTGCCTTGCATAAG
GCCATAATGGTTAAAGGTGTGGATGAAGCAACCATCATTGACATTCTAACTAA
GCGAAACAATGCACAGCGTCAACAGATCAAAGCAGCATATCTCCAGGAAACAG
GAAAGCCCCTGGATGAACACTTAAGAAAGCCCTTACAGGTCACCTTGAGGAG
GTTGTTTTAGCTCTGCTAAAAACTCCAGCGCAATTTGATGCTGATGAACTTCG
TGCTGCCATGAAGGGCCTTGGAACTGATGAAGATACTCTAATTGGGATTTTGG
CATCAAGAACTAACAAAGAAATCAGAGACATTAACAGGGTCTACAGAGAGGAA
CTGAAGAGAGATCTGGCCATAGACATAACCTCAGACACATCTGGAGATTTTCG
GAACGCTTTGCTTTCTCTTACTAAGGGTGACCGATCTGAGGACTTTGGTGTGA
ATGAAGACTTGGCTGATTCAGATGCCAGGGCCTTGTATGAAGCAGGAGAAAGG
AGAAAGGGGACAGACGTAAACGTGTTCAATACCATCCTTACCACCAGAAGCTA
TCCACAACTTCGCAGAGTGTTTCAGAAATACACCAAGTACAGTAAGCATGACA
TGAACAAAGTTCTGGACCTGGAGTTGAAAGGTGACATTGAGAAATGCCTCACA
GCTATCGTGAAGTGCGCCACAAGCAAACCAGCTTTCTTTGCAGAGAAGCTTCA
TCAAGCCATGAAAGGTGTTGGAACTCGCCATAAGGCATTGATCAGGATTATGG
TTTCCCGTTCTGAAATTGACATGAATGATATCAAAGCATTCTATCAGAAGATG
TATGGTATCTCCCTTTGCCAAGCCATCCTGGATGAAACCAAAGGAGATTATGA
GAAATCCTGGTGGCTCTTTGTGGAGGAAACTAAACATTCCCTTGATGGTCTC
AAGCTATGATCAGAAGACTTTAATTATATATTTTCATCCTATAAGCTTAAATA
GGAAAGTTTCTTCAACAGGATTACAGTGTAGCTACCTACATGCTGAAAAATAT
AGCCTTTAAATCATTTTTATATTATAACTCTGTATAATAGAGATAAGTCCATT
TTTAAAAATGTTTTCCCCAAACCATAAAACCCTATACAAGTTGTTCTAGTAA
CAATACATGAGAAAGATGTCTATGTAGCTGAAAATAAAATGACGTCACAAGAC.
```

9. A method for producing a phosphospholipase inhibitor comprising the steps of culturing a host transformed by a recombinant DNA molecule according to claim 3 and collecting said inhibitor.

* * * * *

UNITED STATES PATENT AND TRADEMARK OFFICE
CERTIFICATE OF CORRECTION

PATENT NO. : 4,879,224
DATED : November 7, 1989
INVENTOR(S) : Barbara P. Wallner, R. Blake Pepinsky, Jeffrey L. Garwin It is certified that error appears in the above-identified patent and that said Letters Patent is hereby corrected as shown below:

Column 17, line 16, after "IVI 10042.", insert -- This deposit was transferred to the American Type Culture Collection, Rockville, Maryland, on June 20, 1991, where it is now available under accession number ATCC 68812. --

Signed and Sealed this

Tenth Day of August, 1993

Attest:

MICHAEL K. KIRK

Attesting Officer

Acting Commissioner of Patents and Trademarks